(12) United States Patent
Millar

(10) Patent No.: US 6,817,983 B1
(45) Date of Patent: Nov. 16, 2004

(54) EXTERNAL FLUID-FILLED CATHETER PRESSURE TRANSDUCER

(75) Inventor: Huntly D. Millar, Houston, TX (US)

(73) Assignee: Millar Instruments, Inc., Houston, TX (US)

( * ) Notice: Subject to any disclaimer, the term of this patent is extended or adjusted under 35 U.S.C. 154(b) by 139 days.

(21) Appl. No.: 10/247,807

(22) Filed: Sep. 19, 2002

(51) Int. Cl.[7] ............................................. A61B 5/02
(52) U.S. Cl. .................. 600/488; 600/486; 600/485; 600/561
(58) Field of Search ........................... 600/488, 486, 600/485, 481, 504, 505, 561, 585

(56) References Cited

U.S. PATENT DOCUMENTS

| | | | | |
|---|---|---|---|---|
| 4,557,269 A | * | 12/1985 | Reynolds et al. | 600/488 |
| 4,834,108 A | * | 5/1989 | Vaillancourt | 600/486 |
| 4,873,990 A | * | 10/1989 | Holmes et al. | 600/561 |
| 5,573,007 A | * | 11/1996 | Bobo, Sr. | 600/561 |
| 5,581,038 A | * | 12/1996 | Lampropoulos et al. | 73/727 |
| 6,033,366 A | * | 3/2000 | Brockway et al. | 600/486 |
| 6,394,986 B1 | * | 5/2002 | Millar | 604/264 |

* cited by examiner

*Primary Examiner*—Mary Beth Jones
*Assistant Examiner*—Navin Natnithithadha
(74) *Attorney, Agent, or Firm*—Charles D. Huston; Conley Rose P.C.

(57) ABSTRACT

An external fluid-filled catheter pressure transducer for monitoring fluid pressure characteristics in a vessel in a living body. The external fluid-filled catheter pressure transducer includes an inverted sensor bonded to a hollow carrier so that measuring occurs on the inside of the carrier. The fluid-filled catheter pressure transducer allows pressure measurements to be taken in vessels smaller than 1 mm in diameter. A method for manufacturing an external fluid-filled catheter pressure transducer describes connecting sections of tubing (semi-rigid and flexible) to an inverted sensor module, and providing a reference port for the inverted sensor module.

20 Claims, 3 Drawing Sheets

EXTERNAL FLUID-FILLED CATHETER PRESSURE TRANSDUCER

RELATED APPLICATION

The current application shares some specification and figures with U.S. patent application Ser. No. 10/247,777, entitled "Inverted Sensor Module" filed on Sep. 19, 2002, which is commonly owned or assigned and hereby incorporated by reference.

BACKGROUND OF THE INVENTION

1. Field of the Invention

The present invention relates to pressure-sensing devices. More specifically, the present invention relates to an external fluid-filled catheter apparatus for sensing pressure in a fluid vessel in a living body.

2. Related Art

In the medical field, and particularly in the field of medical research, sensors greatly aid in the evaluation of performance and fluid characteristics of vessels in a living body. Sensors are used to determine characteristics such as fluid pressure, temperature, $O_2$, $CO_2$, sugar levels, and/or pH in blood vessels, lymph vessels, ureters, and ventricles. Medical personnel use this information to evaluate the overall health of a person, and medical researchers use this information to aid in the evaluation of new drugs or procedures.

Typically, sensors are mounted on a catheter for insertion into the vessel. Several patents describe the use of sensors mounted on catheters. However, the use of prior art catheters is not always possible due to the size of the vessel to be monitored in comparison with the catheter. For example, researchers studying cardiac performance in small animals such as mice may encounter blood vessels less than 1 mm in diameter. In these applications, it may not be possible, using prior art sensors, to be able to accurately monitor the cardiac performance directly. In particular, the size of the catheter may be so large that insertion into a blood vessel may block the blood vessel, impair cardiac performance, prevent accurate measurements, and cause injury to the subject. It is therefore desirable to provide an improved method and sensor apparatus for detecting fluid pressures in vessels in a living body. It is further desirable to provide a sensor apparatus capable of being used on small vessels.

In addition, the size of the catheter affects the measuring capability of the sensor. For example, the heart of a mouse beats at a very high rate. The volumetric displacement, however, is very small. If a large volume fluid-filled catheter is used to detect the blood pressure in a mouse blood vessel, the mouse heart may not be strong enough to provide the pressure needed to produce an accurate measurement in a large catheter. It is therefore desirable to provide a sensor apparatus that provides accurate measurements in applications with small volumetric displacement, small pressures, or high frequency pressure waveforms, or all three. It is further desirable to provide a fluid-filled catheter with a high-frequency response.

SUMMARY OF THE INVENTION

The present invention provides accurate measurement of fluid pressure with an inverted sensor module used with a fluid-filled catheter system. Such an invention provides a high-frequency response and allows for measurements in very small vessels less than one millimeter in diameter. The present invention also provides unique advantages relating to the modularity of the catheter pressure transducer.

In one broad respect, the present invention is directed to an external fluid-filled catheter transducer for sensing fluid pressures in body vessels in a living body, said external fluid-filled catheter transducer comprising: an inverted sensor module, said inverted sensor module comprising a sensor module carrier, a sensor mounted to said sensor module carrier such that the diaphragm of said sensor is positioned to measure fluid characteristics on the inside of said inverted sensor module, and communication media connected to said sensor, wherein said sensor is operable to send information to a monitoring device through said communication media; semi-rigid tubing connected to said inverted sensor module and capable of insertion into said living body; flexible tubing connected between said semi-rigid tubing and said inverted sensor module; a reservoir of fluid connected to said inverted sensor module; and a port in said external fluid-filled catheter pressure transducer capable of introducing a reference pressure to said sensor. In an alternative embodiment of the present invention, the external fluid-filled catheter pressure transducer further comprises clamps operable to block the passage of any fluid through any of said sections of flexible tubing. In other embodiments, the semi-rigid tubing comprises polyimide, the flexible tubing comprises transparent silicone rubber, and the inverted sensor carrier comprises rigid tubing. In another embodiment the distal tip of the semi-rigid tubing for insertion into a living body is less than 1 mm in diameter. In other embodiments, the semi-rigid tubing for insertion into a living body is less than 3 cm in length, and the external fluid-filled catheter pressure transducer is operable to be flushed periodically to prevent contamination or clogging by body fluids. In another embodiment, the inverted sensor is operable to detect fluid pressures.

In another broad respect, the present invention is directed to a method for using an external fluid-filled catheter pressure transducer comprising an inverted sensor module, to monitor a fluid pressure in a body vessel, said method comprising the steps of: obtaining an external fluid-filled catheter pressure transducer comprising an inverted sensor module and semi-rigid tubing; priming said external fluid-filled catheter pressure transducer such that substantially no air exists in said external fluid-filled catheter pressure transducer; calibrating said external fluid-filled catheter pressure transducer based on a reference pressure; inserting the distal end of semi-rigid tubing into a target vessel in said living body, wherein said inverted sensor module remains outside said living body; and measuring the fluid pressure present in said target vessel.

In another broad respect, the present invention is directed to a method of manufacturing an external fluid-filled catheter pressure transducer comprising an inverted sensor module, said method comprising the steps of: connecting a first section of tubing to a first end of said inverted sensor module, said first end hereinafter referred to as the distal end, said first section of tubing comprising flexible tubing and semi-rigid tubing; connecting a second section of tubing to a second end of the inverted sensor module, said second end hereinafter referred to as the proximal end, and said second section of tubing comprising flexible tubing and semi-rigid tubing; and connecting said second section of tubing to a fluid-filled reservoir wherein said second section of tubing is capable of introducing a reference pressure on fluid contained within said second section of tubing. In an alternative embodiment, the method further comprises the step of attaching clamps to first and second sections of flexible tubing such that any section or combination of sections may be opened or closed independently or in combination. In another alternative embodiment, the semi-rigid tubing in said first section of tubing is tapered. In yet another alternative embodiment the tapered semi-rigid tubing is drawn.

In a preferred embodiment of the present invention, a fluid-filled catheter with an inverted sensor module comprises a pressure sensor operable to provide a signal representative of fluid pressure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The present invention overcomes the shortcomings of the prior art with a high frequency response external fluid-filled catheter pressure transducer operable to detect pressure characteristics in vessels in a living body.

Figure 1A:
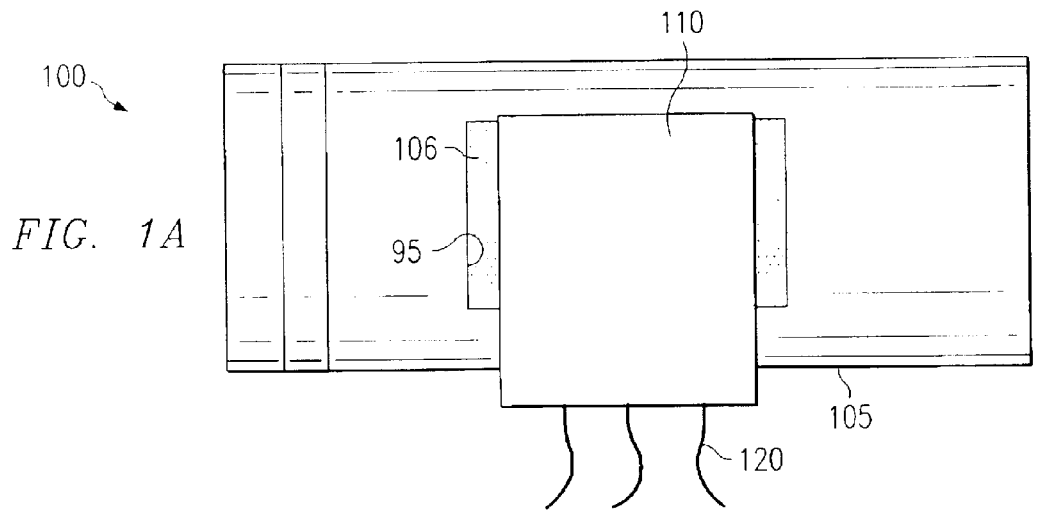
FIG. 1A is a top view of an inverted sensor module for use with an external fluid-filled catheter pressure transducer according to one embodiment of the present invention.
Figure 1B:
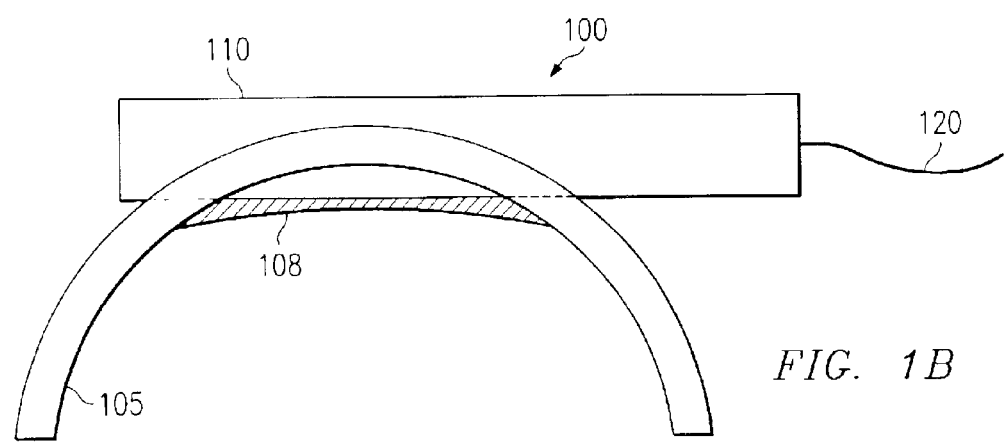
FIG. 1B is an end view of an inverted sensor module for use with an external fluid-filled catheter pressure transducer according to one embodiment of the present invention.
Figure 1C:
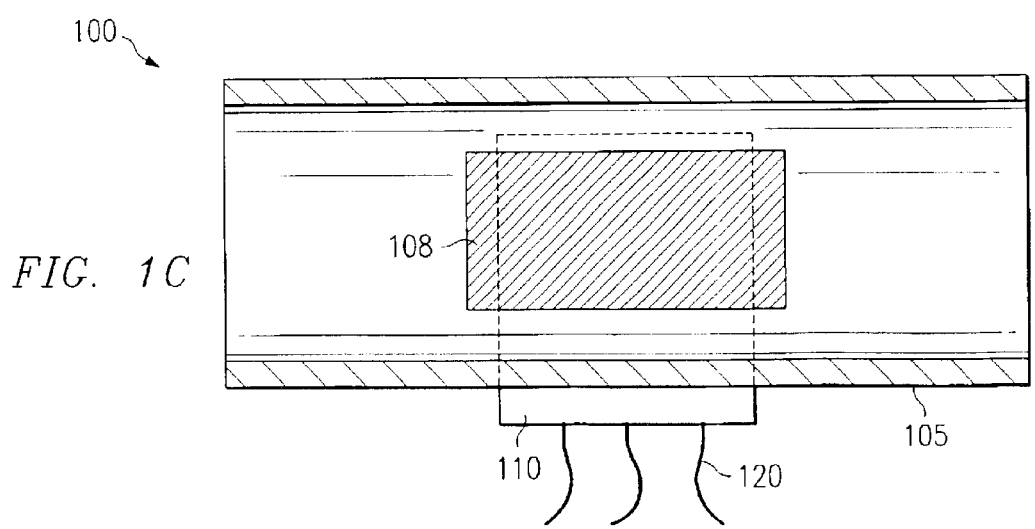
FIG. 1C is a bottom view of an inverted sensor module for use with an external fluid-filled catheter pressure transducer according to one embodiment of the present invention.

Now referring to the figures, FIGS. 1A, 1B, and 1C are top, end, and bottom views of one embodiment of an inverted sensor module 100. The inverted sensor module 100 comprises a carrier 105 having an inner surface and an outer surface. The carrier 105 is preferably constructed of a high strength biocompatible material such as stainless steel, platinum, titanium or ceramic. The inverted sensor module 100 further comprises a sensor 110, which is inverted such that the sensing side faces the inner surface of the carrier 105. The inverted sensor module 100 further comprises wires or other communication media 120.

The sensor carrier 105 is optimally designed for compatibility with a living body. The carrier 105 comprises rigid tubing with a known inner cross-sectional area, and maintains the sensor 110 position in close proximity with the fluid being monitored. In some embodiments, the sensor carrier 105 is manufactured from polyimide tubing. An opening 95 such as a window or slot is machined in the carrier 105 such that the sensor 110, which is attached to the carrier 105, detects fluid characteristics on the inside of the carrier 105. The inner surface of the carrier 105 may be coated or lined with a substance 108 to prevent clotting and to provide a clean flow profile (less turbulence) with substantially no bubble traps. Substance 108 may be an antithrombogenic substance, anti-infective, or contain medications.

The sensor 110 detects physical fluid characteristics such as pressure. The type of sensor 110 used may be resistive, capacitive, or semiconductor-based. Sensors 110 may include, but are not limited to, silicon strain gauge, photoelectric, and fiber-optic sensors. The sensor 110 is held in place on the carrier 105 with an appropriate bonding material 106. A preferred material for bonding a sensor 110 to the carrier 105 is RTV silicone rubber. RTV is a soft, pliant material that does not distort the sensor 110 and provides some electrical isolation of the sensor 110 from the carrier 105.

The communication media 120 provide for communication between the sensor and a monitoring device, as well as power to the sensor. Wires or fiber optic lines may be used for communication and power. The communication media 120 may also be part of any standard electrical communication system, such as a Wheatstone bridge.

Figure 2:
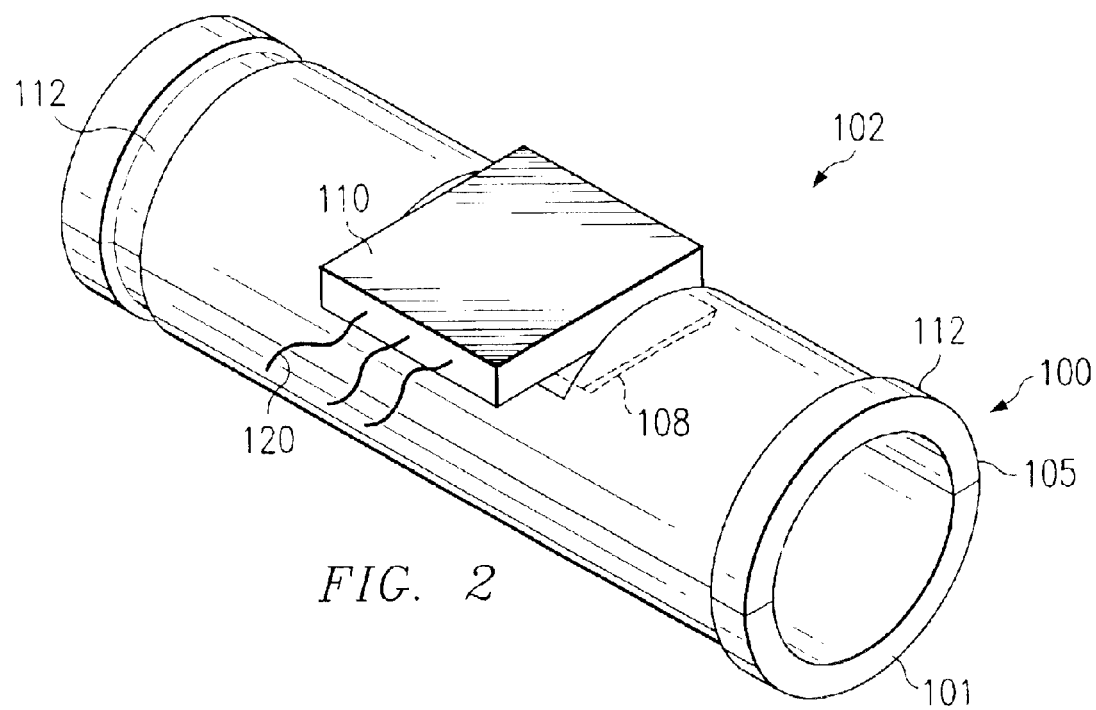
FIG. 2 is an isometric view of an inverted sensor module according to one embodiment of the present invention.

FIG. 2 is an isometric drawing of an inverted sensor module 102 according to one embodiment of the present invention. In this embodiment, inverted sensor module 100 is bonded to rigid tubing section 101. As a result, inverted sensor module 102 is formed, which generally resembles a tube with a lumen, and inverted sensor module 102 is adapted for monitoring characteristics of fluids present in inverted sensor module 102. In a preferred embodiment, the section of tubing 101 and the inverted sensor module carrier 105 are manufactured from the same material, such as polyimide tubing, and are of identical internal diameter to reduce turbulent flow, corrosion, or other effects from using dissimilar materials or varying geometry.

The ends of the inverted sensor module 102 can be attached to semi-rigid or flexible tubing, or to a fluid vessel in a living body. Generally, the ends of the inverted sensor module 102 are attached to tubing using any suitable mechanical or chemical attachment means, such as sutures, clamps, or adhesives.

Additionally, the inverted sensor module 102 may also have a surface feature 112 located at either end for attaching tubing. Surface features 112 include lips, grooves, knurls, or any other surface feature 112 that may be used in combination with any attachment technique to prevent tubing from slipping off the inverted sensor module 102. Ideally, surface feature 112 is such that any attached tubing is not damaged by the attachment to the feature.

Figure 3:
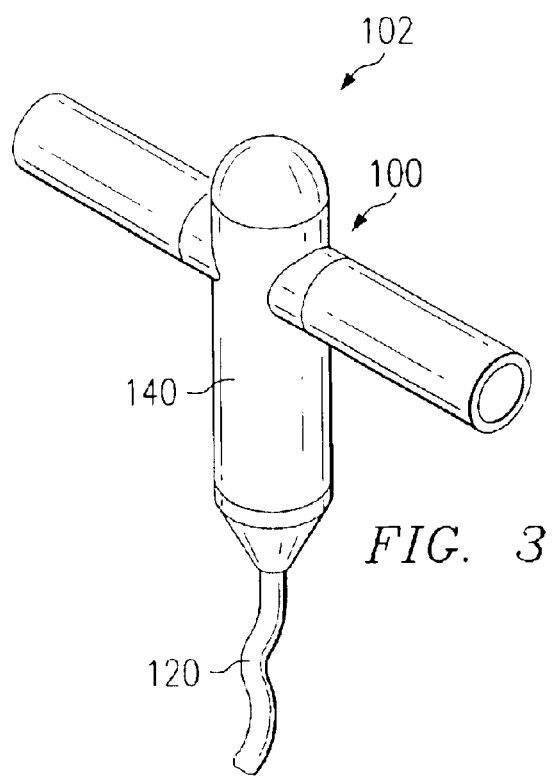
FIG. 3 is an isometric view of an inverted sensor module according to one embodiment of the present invention.

FIG. 3 is an isometric drawing of an inverted sensor module 102, in which a protective housing or covering 140 for the exterior or reference surface of the sensor 110 may be included to protect sensor 110 and communication media 120 from damage. The protective housing 140 may be bonded to the inverted sensor module 102 using RTV silicone rubber, a biocompatible epoxy, or any other adhesive, mechanical or thermal technique.

Figure 4:
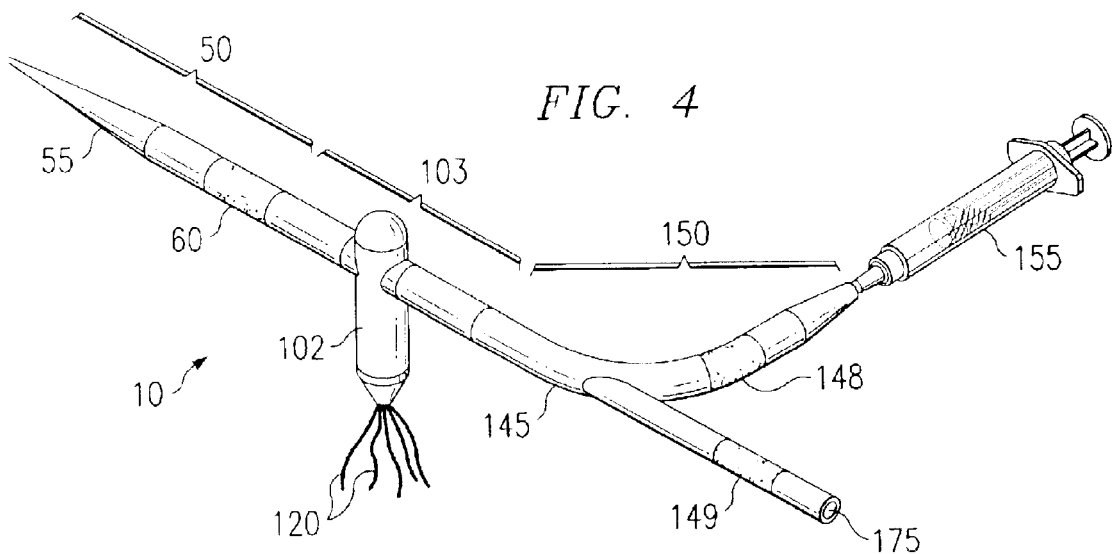
FIG. 4 is an isometric view of an external fluid-filled catheter pressure transducer in accordance with one embodiment of the present invention.

The embodiment shown in FIG. 4 allows the benefits of an inverted sensor module 102 (such as shown in FIGS. 2 and 3) to be applied to an external fluid-filled catheter pressure transducer 10. In the preferred embodiment shown in FIG. 4, an external fluid-filled catheter pressure transducer 10 includes an inverted sensor module 102 as described above, semi-rigid tubing sections 55 and 145, flexible tubing sections 60, 148, and 149, a fluid reservoir 155, and a port 175 to an external pressure reference.

The inverted sensor module 102 may have surface features as described above with respect to FIG. 2 at either end to facilitate attachment to various types of vessels or tubing to the inverted sensor module 102 Furthermore, the surface features 112 described above may be used to attach manufactured vessels such as tubing without departing in scope from the present invention. In addition to those mentioned above, other chemical, mechanical, and thermal techniques may be used to attach semi-rigid or flexible tubing to the inverted sensor module 102.

The flexible tubing sections 60, 148, and 149 and the semi-rigid tubing sections 55 and 145 may be, but are not required to be, transparent. Advantageously, transparent tubing allows monitoring personnel to visually check for bubbles in the system or diffusion of unwanted particles from the body into the system. In a preferred embodiment, the semi-rigid tubing is manufactured with a polyimide composition.

A small section of flexible tubing 60 and a section of semi-rigid tubing 55 are connected end-to-end to one end (hereinafter called the distal end 50) of the inverted sensor module. The semi-rigid tubing 55 is preferably tapered in a smooth manner so that fluid may flow in either direction of the semi-rigid tubing 55 without bubble traps or bubble formation due to pressure variation. In a preferred embodiment, semi-rigid tubing 55 is drawn to provide the smooth tapered profile. The semi-rigid tubing 55 is long enough so that when the distal tip 50 is inserted into a vessel for monitoring, the flexible tubing section 60 is external to the body being monitored. However, the semi-rigid tubing 55 is ideally short enough to minimize the fluid volume contained in the semi-rigid tubing 55. In a preferred embodiment, the length of the semi-rigid tubing 55 is less than 3 cm. An external fluid-filled catheter pressure transducer 10 according to the present invention maintains a high-frequency response due in part to the smaller volume of fluid. Such an external fluid-filled catheter pressure transducer 10 is desirable in applications characterized by small pressures, particularly research on cardiac performance in mice and earthworms. The flexible tubing 60 is in-line between the semi-rigid tubing 55 and the inverted sensor module 102 and is capable of collapsing under a force so that the semi-rigid tubing 55 may be closed off from the inverted sensor module 102. The force required to collapse the flexible tubing 60 should essentially not damage the flexible tubing 60. In a preferred embodiment, the flexible tubing 60 is a silicone rubber compound. In a preferred embodiment, small hemostat clamps or alligator clips (not shown) provide enough force to collapse the flexible tubing 60 without damage.

The other (hereinafter, proximal) end of the inverted sensor module 102 attaches to a section of tubing 150, which is in fluid communication with a reservoir 155 and a reference port 175. This section of tubing 150 includes semi-rigid tubing 145 with sections of flexible tubing (148 and 149) in-line for the purpose of closing off the fluid flow from the reservoir 155 to the inverted sensor module 102, and for closing off the reference port 175 from the inverted sensor module 102. Hemostat clamps or alligator clips similar to those used to close off the flexible tubing 55 on the distal side 50 may also be used to close off the flexible tubing 148 and 149 on the proximal side 150 for similar reasons. The use of any clamp or combination of clamps to close off any section or combination of sections of this embodiment are described more in the description of FIG. 5. The use of clamps is advantageous over the use of fittings or stopcocks due to the minimal damping effect of a clamped system; for reducing the volumetric displacement of the system; and because Luer fittings and stopcocks are sites where bubbles can form. The presence of compressible air bubbles in a pressure sensing system lessens the frequency response.

Figure 5:
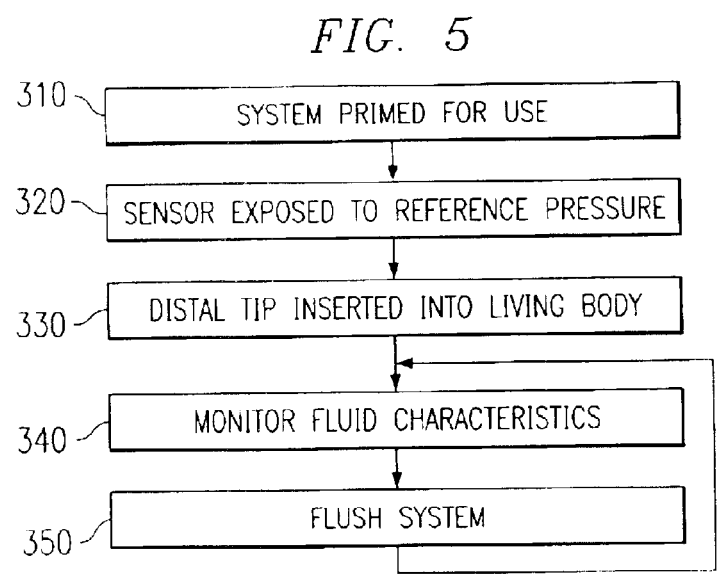
FIG. 5 is a flowchart of steps in the process for sensing pressures in a living body using an external fluid-filled catheter pressure transducer.

Now referring to FIG. 5, a method is described for monitoring a vessel in a living body, utilizing an external fluid-filled catheter pressure transducer 10 with an inverted sensor module 102. For illustrative purposes only, a method for sensing pressure and a pressure sensor are described. In the embodiment described here, the external fluid-filled catheter pressure transducer 10 is initially connected to a fluid reservoir 155, but clamps on flexible tubing sections 60 and 149 close all proximal tubing sections.

In step 310, the external fluid-filled catheter pressure transducer 10 is primed for use. The reference port 175 is closed off from the rest of the tubing 145. Generally, an alligator clip or hemostat clamp applied to the appropriate section of flexible tubing 149 closes the section of tubing to the reference port 175. The clamp on the flexible tubing section 148 to the reservoir 155 is removed, whereby fluid from the reservoir 155 flows through the proximal tubing 150, through the inverted sensor module 102, and through the distal tubing 50 to prime the external fluid-filled catheter pressure transducer 10. Priming the external fluid-filled catheter pressure transducer 10 optimally results in no bubbles in the external fluid-filled catheter pressure transducer 10.

In step 320, the sensor 110 is exposed to a reference pressure through reference port 175 once the external fluid-filled catheter pressure transducer 10 is primed. The tubing 150 from the reservoir 155 is closed off by clamping the appropriate flexible tubing section 148 and the tubing 149 to the reference port 175 is opened, thereby exposing the fluid to a reference pressure. Again, alligator clips or hemostat clamps applied to or removed from appropriate sections of flexible tubing 148 and 149 successfully close or open sections of tubing. Once a reference pressure has been established, the tubing 149 to the reference pressure 175 is closed off.

In step 330, the distal tip 50 of the external fluid-filled catheter pressure transducer 10 is inserted into a vessel in a living body. Generally, it is desired that flexible tubing section 60 remain outside the body so that clamps may be applied to tubing section 50 if needed.

In step 340, monitoring of fluid characteristics begins. In this example, fluid pressure measurements are transmitted from the pressure sensor 110 on the inverted sensor module 102, which is located external to the body in this embodiment, to a monitoring device (not shown).

At various times, it may be desirable to flush the external fluid-filled catheter pressure transducer 10 to prevent body fluid from contacting the sensor 110 or contaminating the external fluid-filled catheter pressure transducer 10 or living body in other ways. In step 350, flushing the external fluid-filled catheter pressure transducer 10 generally involves the procedures of step 310, except the flushing may take place with the distal tip 50 of the external fluid-filled catheter pressure transducer 10 still inserted in the body. Furthermore, the flexible tubing sections 148, 149 and 60 may be clamped or sealed off by any tool that does not allow fluid flow through the flexible tubing section 148, 149 and 60 or allow bubbles to form in the tubing.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as exemplary embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. An external fluid-filled catheter transducer for sensing fluid pressure in a body vessel in a living body, said fluid-filled catheter transducer comprising:

an inverted sensor module, said inverted sensor module comprising a sensor module carrier, a sensor mounted to said sensor module carrier such that the diaphragm of said sensor is positioned to sense fluid characteristics inside of said inverted sensor module, and communication media connected to said sensor, wherein said sensor is operable to send information to a monitoring device through said communication media;

semi-rigid tubing connected to said inverted sensor module and capable of insertion into said living body;

flexible tubing connected between said semi-rigid tubing and said inverted sensor module;

a reservoir of fluid connected to said inverted sensor module; and a port located in said external catheter and capable of introducing a reference pressure to said sensor.

2. The external fluid-filled catheter transducer of claim 1, further comprising clamps operable to block the passage of any fluid through any of said sections of flexible tubing.

3. The external fluid-filled catheter transducer of claim 1, wherein said semi-rigid tubing comprises polyimide.

4. The external fluid-filled catheter transducer of claim 1, wherein said flexible tubing comprises silicone rubber.

5. The external fluid-filled catheter transducer of claim 1, wherein said sensor module carrier comprises rigid tubing.

6. The external fluid-filled catheter transducer of claim 1, wherein a distal tip of said semi-rigid tubing for insertion into a living body is less than 1 mm in diameter.

7. The external fluid-filled catheter transducer of claim 6, wherein said distal tip of said semi-rigid tubing is tapered.

8. The external fluid-filled catheter transducer of claim 7, wherein said semi-rigid tubing is drawn.

9. The external fluid-filled catheter of claim 1, wherein said semi-rigid tubing for insertion into a living body is loss than 3 cm in length.

10. The external fluid-filled catheter transducer of claim 1, wherein said external fluid-filled catheter transducer is operable to be flushed periodically to prevent contamination or clogging by body fluids.

11. The external fluid-filled catheter transducer of claim 1, wherein said fluid-filled catheter transducer is operable to expose said sensor to a reference pressure.

12. The external fluid-filled catheter transducer of claim 1, wherein said sensor is operable to detect fluid pressure.

13. The external fluid-filled catheter transducer of claim 1, wherein said sensor is a resistive type sensor.

14. A method for determining a fluid pressure in a vessel inside a living body, comprising the steps of:

obtaining an external fluid-filled catheter pressure transducer comprising an inverted sensor module having a distal end and a proximal end, wherein said distal end comprises tapered semi-rigid tubing, wherein said proximal end comprises a first section of tubing coupled to a fluid reservoir and a second section of tubing coupled to a reference port, and wherein said first and second sections of tubing each comprise flexible tubing and semi-rigid tubing;

priming said external fluid-filled catheter pressure transducer such that substantially no air exists in said external fluid-filled catheter pressure transducer by allowing fluid to flow through the flexible tubing of the first section, while passage through the flexible tubing of the second section is closed off;

calibrating said external fluid-filled catheter pressure transducer based on a reference pressure obtained by opening the passage through the flexible tubing of the second section;

inserting a distal end of said tapered semi-rigid tubing into a target vessel in said living body, wherein said external fluid-filled catheter pressure transducer remains outside said living body; and determining the fluid pressure present in said target vessel.

15. The method as recited in claim 14, wherein the step of priming further comprises attaching a clamp to the flexible tubing of the second section to close off the passage therethrough.

16. The method as recited in claim 15, wherein the step of calibrating further comprises removing the clamp from the flexible tubing of the second section to open the passage therethrough after another clamp is attached to the flexible tubing of the first section.

17. The method as recited in claim 16, wherein after said step of calibrating and before said step of inserting the method further comprises re-attaching the clamp to the flexible tubing of the second section.

18. The method as recited in claim 17, further comprising flushing said external fluid-filled catheter pressure transducer while the distal end of said tapered semi-rigid tubing is inserted within the target vessel, wherein said flushing comprises removing the clamp from the flexible tubing of the first section to allow fluid to flow therethrough.

19. A method of manufacturing an external fluid-filled catheter pressure transducer comprising an inverted sensor module, said method comprising the steps of:

connecting a first section of tubing to a first end of said inverted sensor module, said first end hereinafter referred to as the distal end, said first section of tubing comprising flexible tubing and semi-rigid tubing; and connecting a second section of tubing to a second end of the inverted sensor module, said second end hereinafter referred to as the proximal end, and said second section of tubing comprising flexible tubing and semi-rigid tubing; and wherein said second section of tubing has a reference port capable of introducing a reference pressure on fluid contained within said external fluid-filled catheter pressure transducer; and wherein said second section of tubing is capable of connecting to a fluid-filled reservoir.

20. The method of claim 19, further comprising the step of attaching clamps to said sections of flexible tubing such that any section or combination of sections may be opened or closed independently or in combination.

* * * * *